(12) United States Patent
Garrison et al.

(10) Patent No.: US 7,909,862 B2
(45) Date of Patent: Mar. 22, 2011

(54) DELIVERY SYSTEMS AND METHODS FOR DEPLOYING EXPANDABLE INTRALUMINAL MEDICAL DEVICES

(75) Inventors: Michael L. Garrison, Indianapolis, IN (US); Brian C. Case, Bloomington, IN (US); Andrew K. Hoffa, Bloomington, IN (US); Jacob A. Flagle, Bloomington, IN (US); Dusan Pavcnik, Portland, OR (US)

(73) Assignee: Cook Medical Technologies LLC, Bloomington, IN (US)

( * ) Notice: Subject to any disclaimer, the term of this patent is extended or adjusted under 35 U.S.C. 154(b) by 662 days.

(21) Appl. No.: 10/804,386

(22) Filed: Mar. 19, 2004

(65) Prior Publication Data

US 2004/0225322 A1 Nov. 11, 2004

Related U.S. Application Data

(60) Provisional application No. 60/455,914, filed on Mar. 19, 2003.

(51) Int. Cl.
*A61F 2/06* (2006.01)
*A61M 29/00* (2006.01)

(52) U.S. Cl. ...................... 623/1.11; 606/200

(58) Field of Classification Search ................ 606/159, 606/200, 110, 127, 198, 213, 113–114; 623/1.1, 623/2.1, 902–904, 11.11
See application file for complete search history.

(56) References Cited

U.S. PATENT DOCUMENTS

| | | | |
|---|---|---|---|
| 2,649,092 A | 8/1953 | Wallace | |
| 4,790,812 A | 12/1988 | Hawkins, Jr. et al. | |
| 5,509,900 A | 4/1996 | Kirkman | |
| 5,534,007 A * | 7/1996 | St. Germain et al. | 623/1.11 |
| 5,643,171 A | 7/1997 | Bradshaw et al. | |
| 5,658,301 A | 8/1997 | Lemaitre et al. | |
| 5,718,684 A | 2/1998 | Gupta | |
| 5,769,821 A | 6/1998 | Abrahamson et al. | |
| 5,807,398 A * | 9/1998 | Shaknovich | 623/1.11 |
| 5,938,582 A | 8/1999 | Ciamacco, Jr. et al. | |
| 6,071,263 A * | 6/2000 | Kirkman | 604/104 |
| 6,117,386 A | 9/2000 | Stiger | |

(Continued)

FOREIGN PATENT DOCUMENTS

CA 2 403 030 A1 3/2003

(Continued)

OTHER PUBLICATIONS

Non-final Office Action issued on Sep. 15, 2009 U.S. Appl. No. 11/800,292.

*Primary Examiner* — Todd E Manahan
*Assistant Examiner* — Diane Yabut
(74) *Attorney, Agent, or Firm* — Buchanan Nipper

(57) ABSTRACT

Methods and devices for delivering and deploying expandable intraluminal medical devices at a desired point of treatment within a body vessel are provided. A delivery device is provided, inserted into a body vessel, and navigated through the vessel to place an associated expandable intraluminal medical device at a desired point of treatment. Once the desired location is reached, an elongate member on which the expandable intraluminal medical device is disposed is spaced from a wall surface of the body vessel using an expandable wire basket, balloon, or other suitable structure. The expandable intraluminal medical device is deployed from the delivery system, which can ultimately be withdrawn from the body vessel.

5 Claims, 12 Drawing Sheets

U.S. PATENT DOCUMENTS

| | | |
|---|---|---|
| 6,338,735 B1 | 1/2002 | Stevens |
| 6,383,206 B1 * | 5/2002 | Gillick et al. ............... 606/200 |
| 6,447,530 B1 | 9/2002 | Ostrovsky et al. |
| 6,450,988 B1 | 9/2002 | Bradshaw |
| 6,485,500 B1 | 11/2002 | Kokish et al. |
| 6,491,662 B1 | 12/2002 | Liprie et al. |
| 6,500,182 B2 | 12/2002 | Foster |
| 6,508,833 B2 | 1/2003 | Pavcnik et al. |
| 6,558,349 B1 | 5/2003 | Kirkman |
| 6,629,987 B1 | 10/2003 | Gambale et al. |
| 6,679,860 B2 | 1/2004 | Stiger |
| 6,692,484 B1 | 2/2004 | Karpiel et al. |
| 6,695,858 B1 | 2/2004 | Dubrul et al. |
| 6,918,929 B2 | 7/2005 | Udipi et al. |
| 6,932,829 B2 * | 8/2005 | Majercak ............... 606/198 |
| 7,144,408 B2 * | 12/2006 | Keegan et al. ............ 606/200 |
| 2001/0039450 A1 * | 11/2001 | Pavcnik et al. ............ 623/1.24 |
| 2003/0032977 A1 | 2/2003 | Brady |
| 2003/0050694 A1 | 3/2003 | Yang et al. |
| 2004/0087965 A1 * | 5/2004 | Levine et al. ............ 606/108 |
| 2004/0087996 A1 | 5/2004 | Gambale et al. |
| 2005/0171592 A1 | 8/2005 | Majercak |

FOREIGN PATENT DOCUMENTS

| | | |
|---|---|---|
| WO | WO 01/26726 A1 | 4/2001 |

* cited by examiner

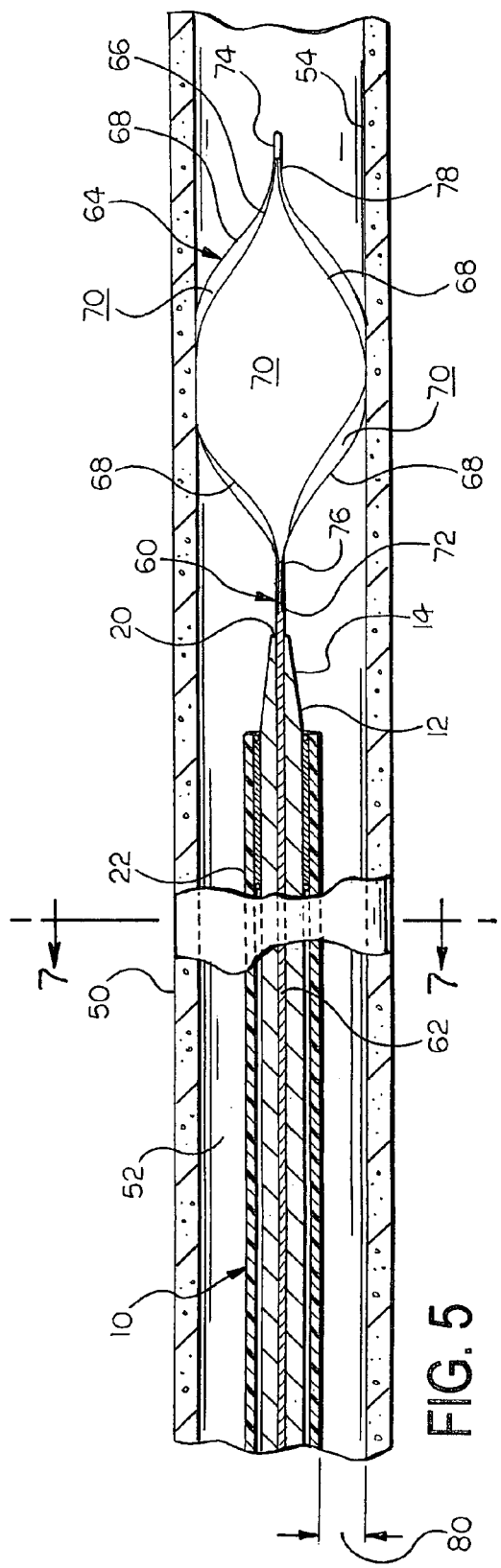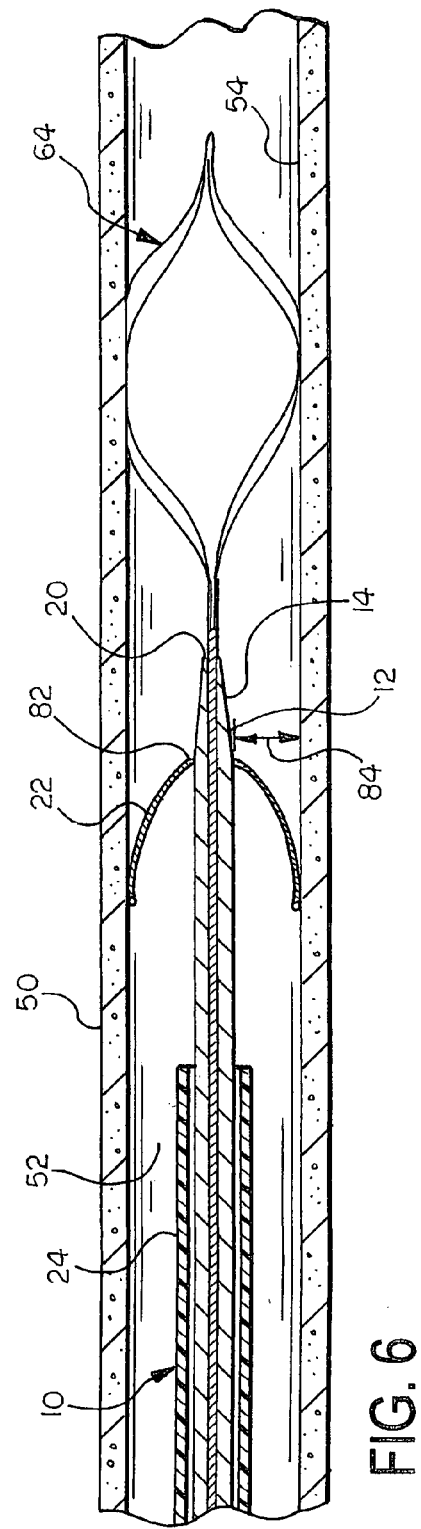

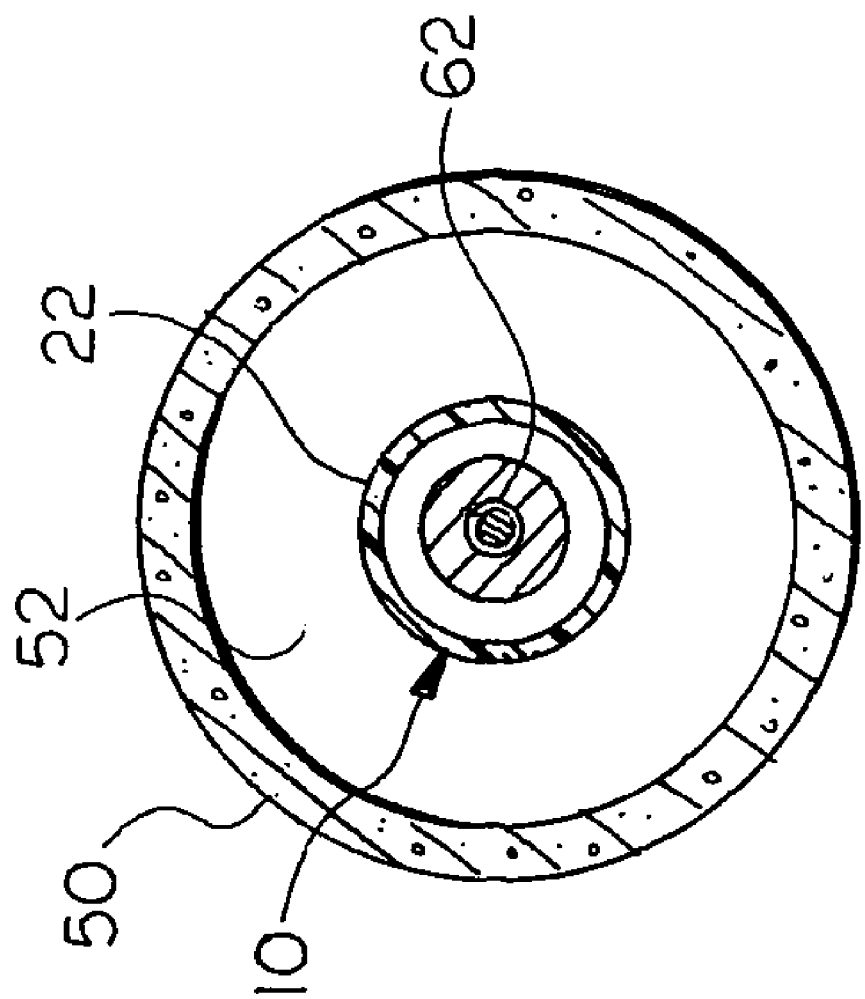

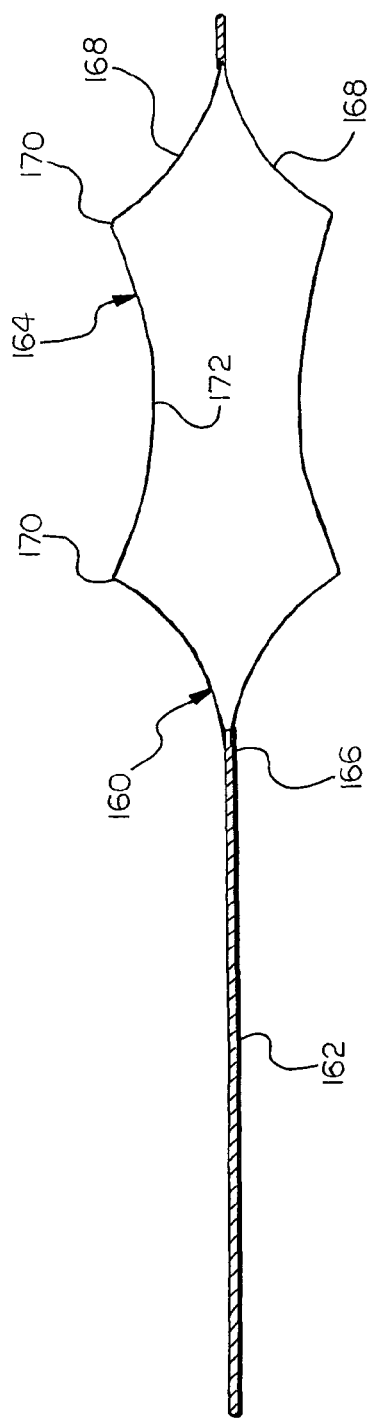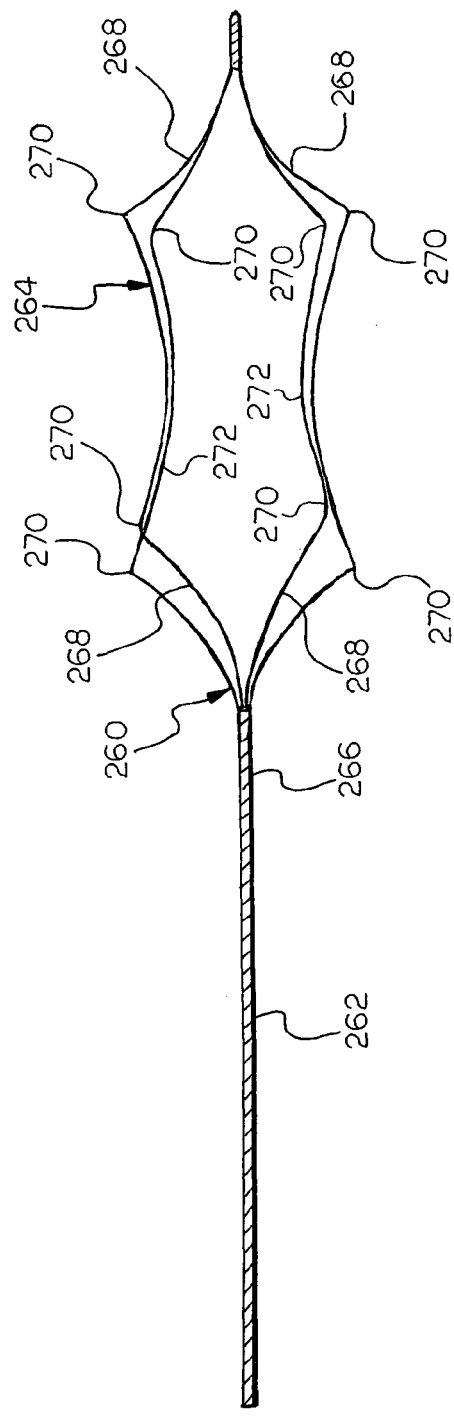

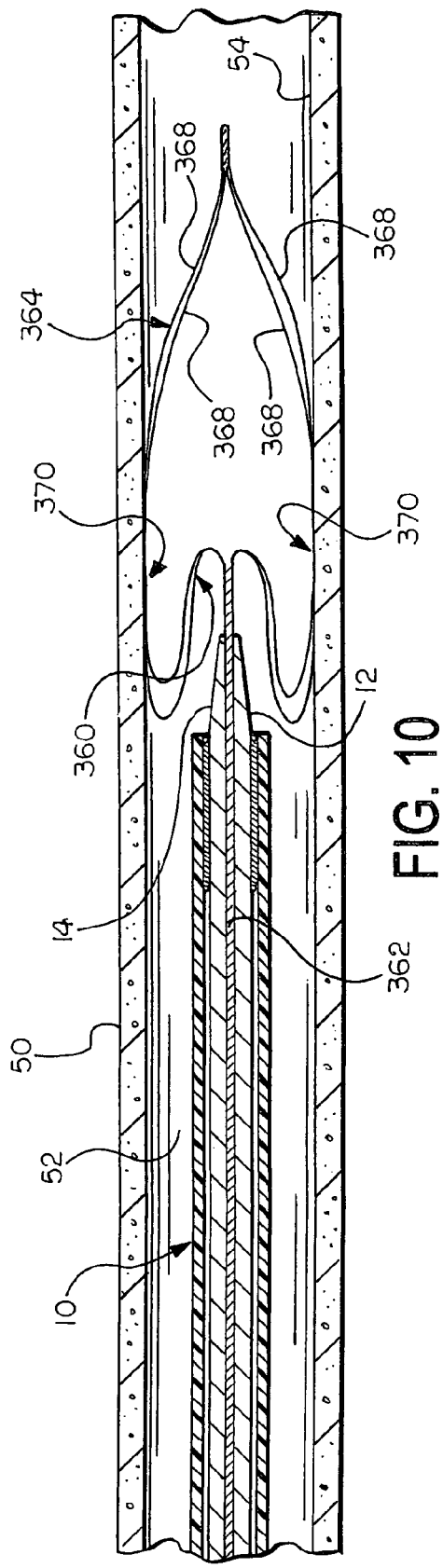

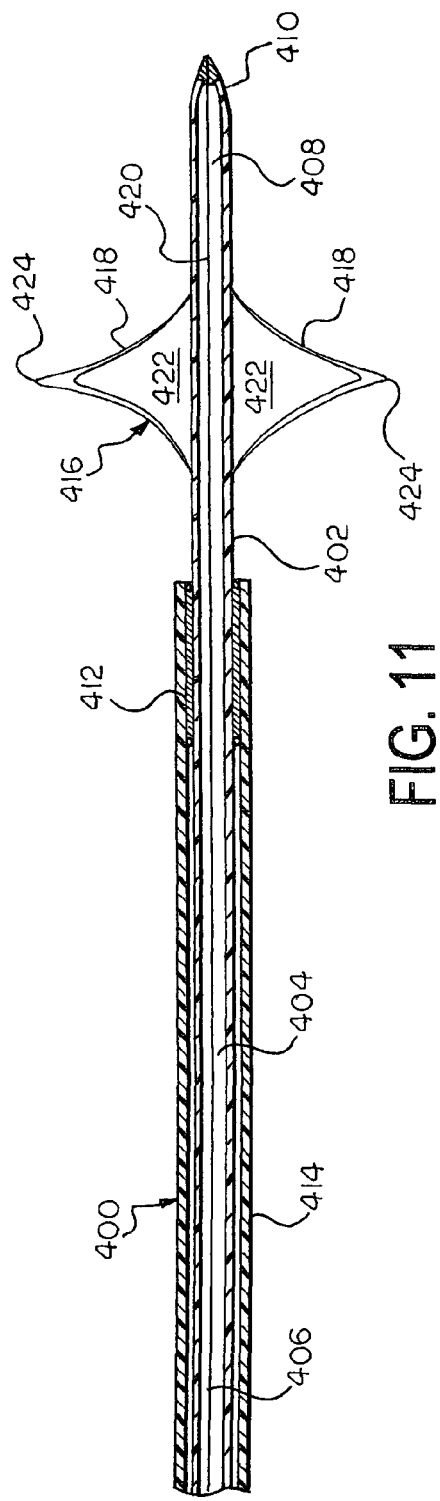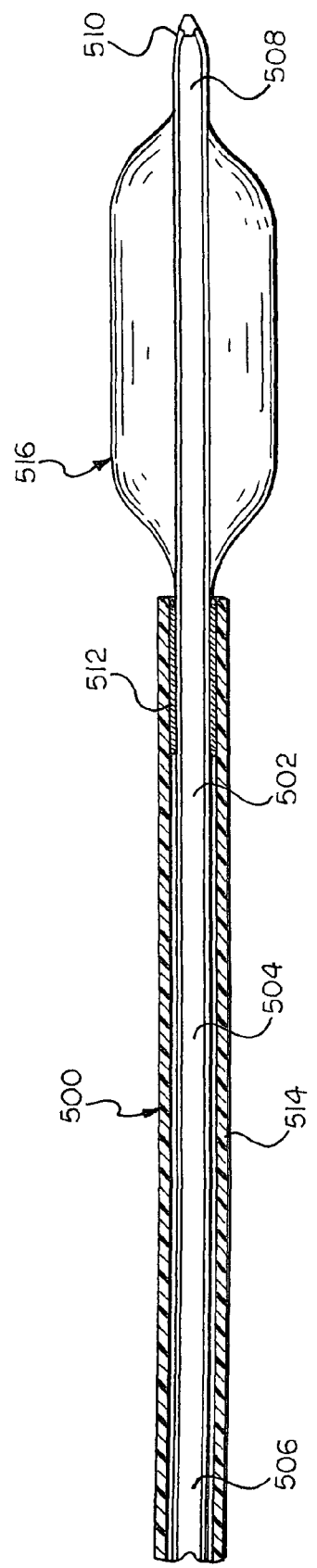
FIG. 11
FIG. 12

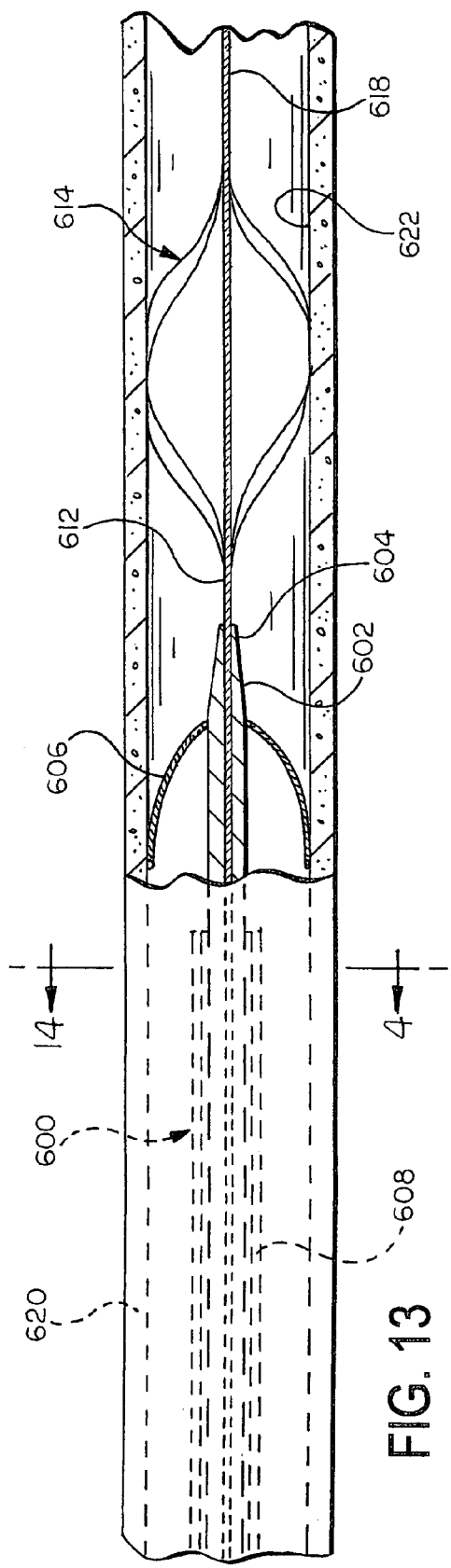
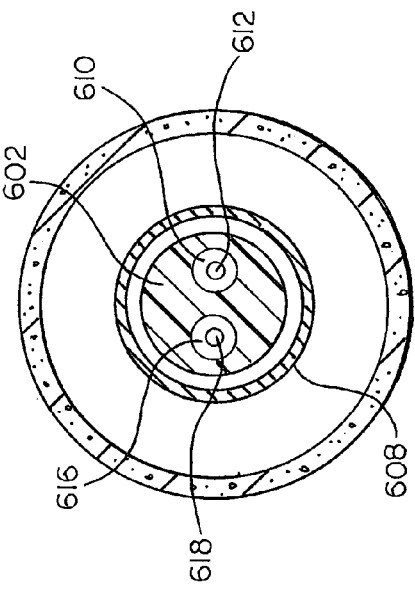
FIG. 13
FIG. 14

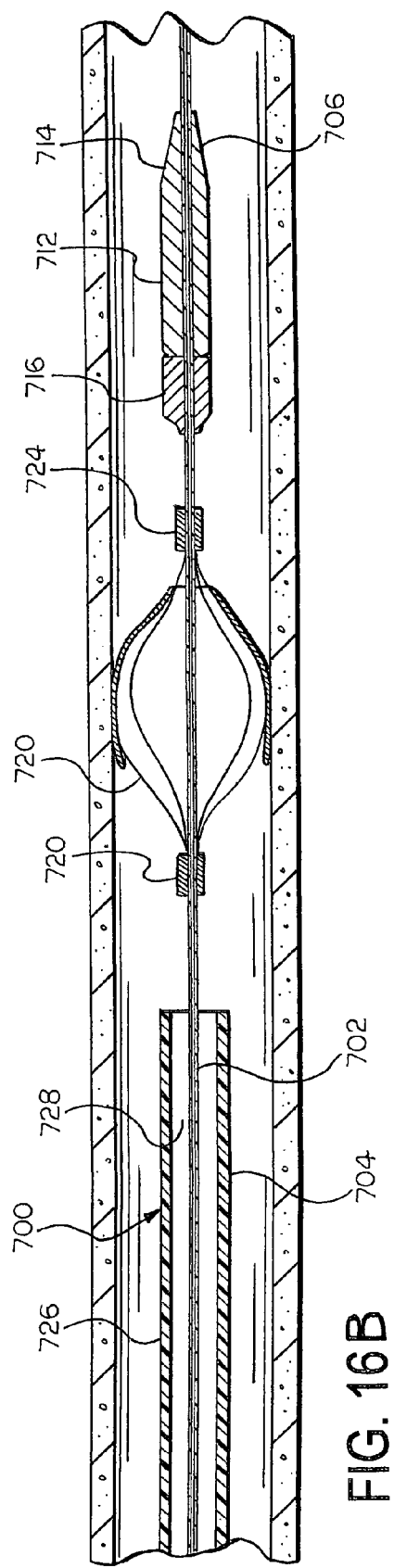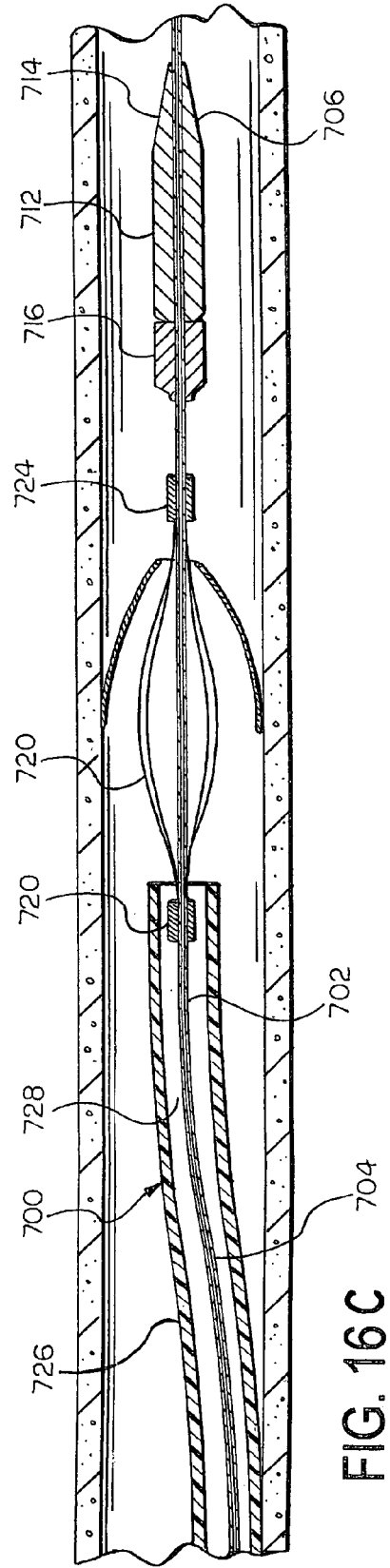
FIG. 16B
FIG. 16C

DELIVERY SYSTEMS AND METHODS FOR DEPLOYING EXPANDABLE INTRALUMINAL MEDICAL DEVICES

CROSS-REFERENCE TO RELATED APPLICATION

This application claims priority to U.S. Provisional Application Ser. No. 60/455,914 filed on Mar. 19, 2003, the entire disclosure of which is hereby incorporated herein in its entirety.

FIELD OF THE INVENTION

The invention can be applied to the field of medical devices. Particular embodiments of the invention can be applied to the field of delivery systems for deploying expandable intraluminal medical devices.

BACKGROUND

Expandable intraluminal medical devices are commonly used in a variety of medical procedures. For example, expandable stents are commonly used to provide intraluminal support to a body vessel, such as a coronary artery. Minimally invasive techniques are frequently used to delivery such medical devices to a desired point of treatment and to deploy the medical device at the point of treatment. In these techniques, a delivery system is used to carry the expandable intraluminal medical device through a body vessel and to the point of treatment. Once the point of treatment is reached, the expandable intraluminal medical device is deployed from the delivery system, which is subsequently withdrawn from the point of treatment and, ultimately, the body vessel.

Some expandable intraluminal medical devices include a functional mechanism that is sensitive to orientation within a body vessel relative to the interior wall surface of the body vessel. The expandable intraluminal medical device may include a functional mechanism that may not perform as desired if the functional mechanism is disposed adjacent a wall surface of the body vessel following deployment. For example, some prosthetic venous valves include a valve orifice that may not function as desired if the valve orifice is orientated grossly toward an interior wall surface of a body vessel. The valve orifice could be tilted toward the wall, which might affect an ability of the valve to regulate fluid flow through the device. Further, the leaflet or leaflets of a prosthetic venous valve with a valve orifice oriented grossly toward a vessel wall surface may be obstructed or otherwise affected by such orientation. Also, intraluminal filters provide a functional mechanism, typically a plurality of interwoven members, for trapping objects flowing through a vessel. The performance of the filter may be affected if the interwoven members, or a portion thereof, are oriented grossly toward an interior wall surface of a body vessel.

Prior art delivery systems may not provide a desirable system for deploying such expandable intraluminal medical devices. Accordingly, there is a need for improved delivery systems and methods of delivering expandable intraluminal medical devices.

SUMMARY OF EMBODIMENTS OF THE INVENTION

The invention provides methods for delivering and deploying expandable intraluminal medical devices within a body vessel. One method comprises providing a delivery system that includes an elongate member with an expandable intraluminal medical device disposed about a portion of the elongate member. In another step, the method includes inserting the distal end of the elongate member into a body vessel. In another step, the method includes advancing the distal end of the elongate member through the body vessel and to a desired point of treatment. In another step, the method includes spacing a portion of the elongate member from a wall surface of the body vessel. In another step, the method includes deploying the expandable intraluminal medical device from the elongate member. In another step, the method includes withdrawing the elongate member from the body vessel.

The invention also provides delivery systems. In one embodiment of the invention, a delivery system includes an elongate member that defines a lumen. An expandable intraluminal medical device is disposed about a portion of the elongate member. A sheath is circumferentially disposed about a portion of the elongate member and the expandable intraluminal medical device. The sheath is moveable along the elongate member. An ancillary device is disposed in the lumen and includes an expandable basket which expands upon exiting the lumen of the elongate member. The expansion of the basket spaces a portion of the elongate member from a wall surface of a body vessel within which the delivery system is used to deploy the expandable intraluminal medical device.

In another embodiment, the elongate member of the delivery system includes a means for spacing a portion of the elongate member from a wall surface of a body vessel within which the delivery system is used to deploy an expandable intraluminal medical device. The means for spacing can be any suitable structure, including a Malecot assembly and an inflatable balloon. In this embodiment, the expandable intraluminal medical device is disposed about a portion of the elongate member and is spaced from the means for spacing.

While the invention is defined by the claims, an understanding of the invention can be gained from the detailed description of exemplary embodiments, which appears below, and the appended drawings.

BRIEF DESCRIPTION OF THE DRAWINGS

FIG. 5 is a sectional view of a delivery system according to an embodiment of the invention shown within a body vessel.

FIG. 6 is a sectional view of the delivery system illustrated in FIG. 5 following expansion of an associated expandable intraluminal medical device.

FIG. 7 is a cross-sectional view of the delivery system and vessel illustrated in FIG. 5, taken along line 7-7.

FIG. 8 is an elevational view of an ancillary delivery device according to an embodiment of the invention.

FIG. 9 is an elevational view of an ancillary delivery device according to an embodiment of the invention.

FIG. 10 is a sectional view of a delivery system according to an embodiment of the invention shown within a body vessel.

FIG. 11 is a sectional view of a delivery system according to an embodiment of the invention.

FIG. 12 is a sectional view of a delivery system according to an embodiment of the invention.

FIG. 13 is a partial sectional view of a delivery system according to an embodiment of the invention shown within a body vessel.

FIG. 14 is a cross-sectional view of the delivery system and vessel illustrated in FIG. 13, taken along line 14-14.

FIG. 16B is a sectional view of the delivery system illustrated in FIG. 15 shown within a body vessel and at a subsequent stage of deployment of an expandable intraluminal medical device.

FIG. 16C is a sectional view of the delivery system illustrated in FIG. 15 shown within a body vessel and at a subsequent stage of deployment of an expandable intraluminal medical device.

DETAILED DESCRIPTION OF EXEMPLARY EMBODIMENTS OF THE INVENTION

The following detailed description and the appended drawings describe and illustrate various exemplary embodiments of the invention. The description and drawings serve to enable one skilled in the art to make and use the invention, and are not intended to limit the scope of the invention in any manner.

Figure 1:
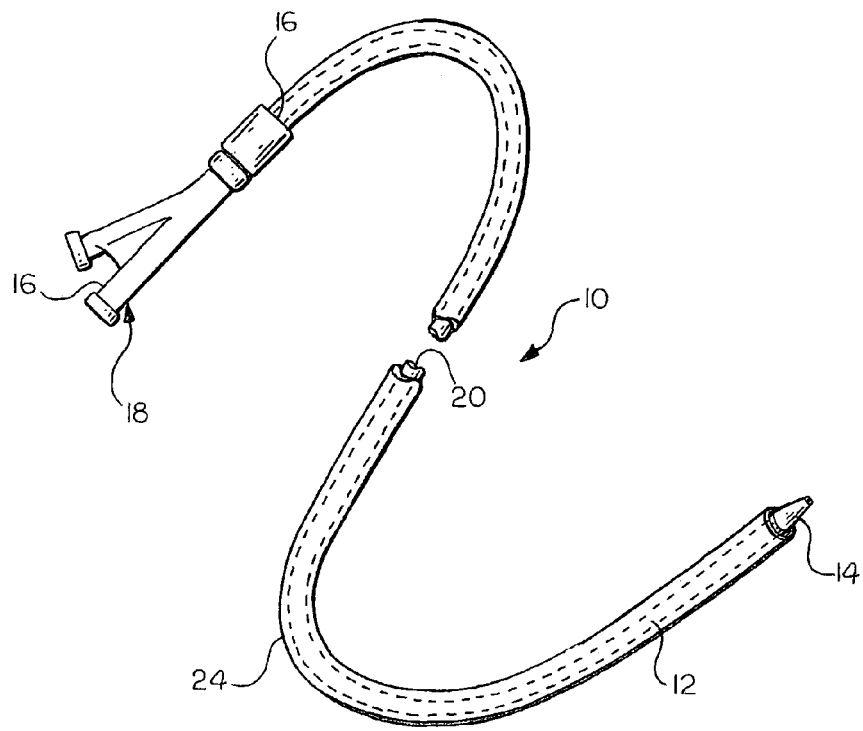
FIG. 1 is a perspective view, partially broken away, of a prior art delivery system.
Figure 2:
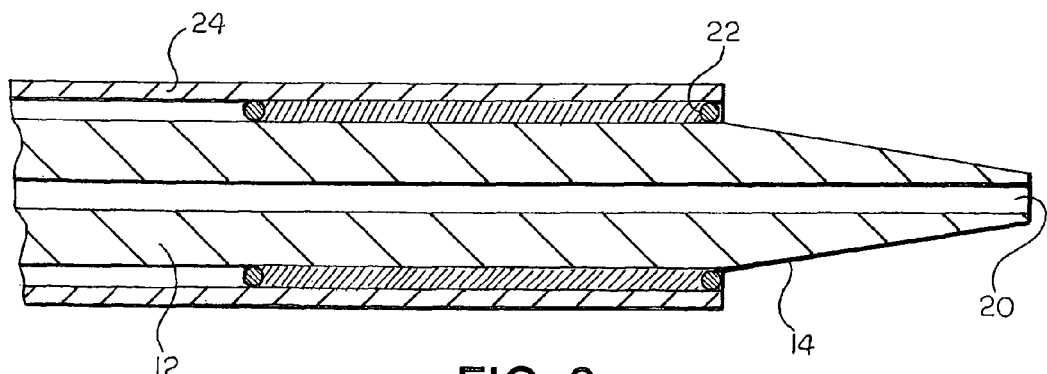
FIG. 2 is a partial sectional view of the prior art delivery system illustrated in FIG. 1.
Figure 3:
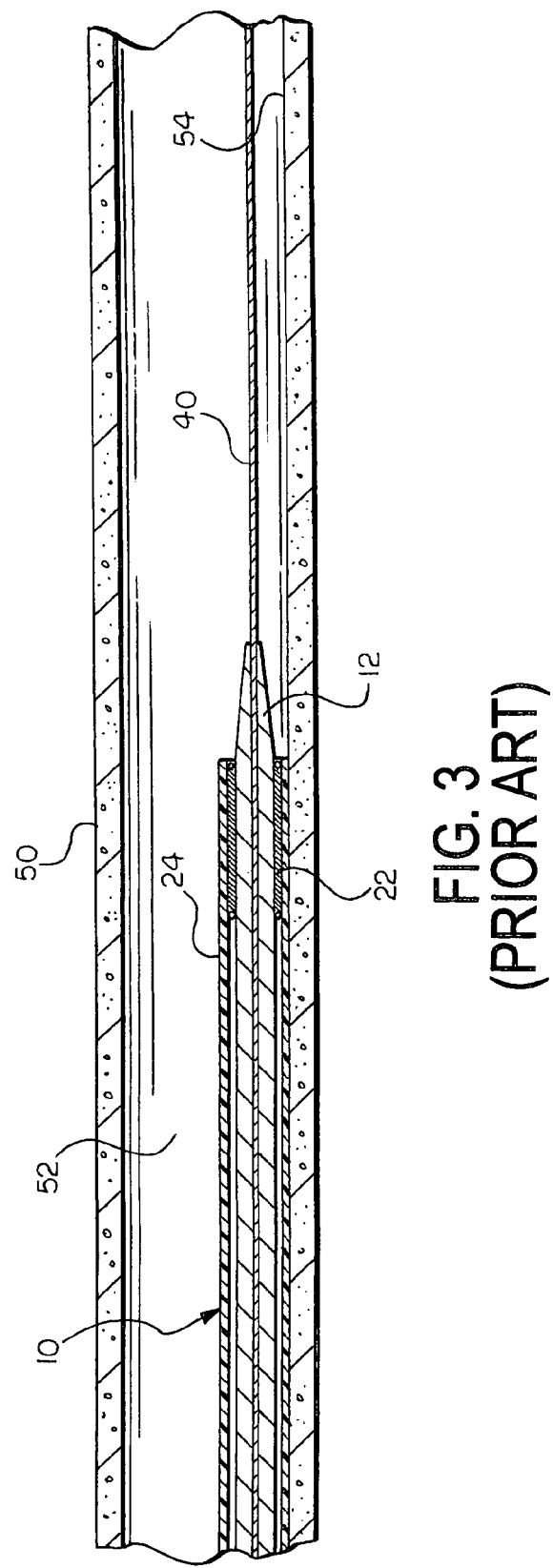
FIG. 3 is a sectional view of the prior art delivery system illustrated in FIG. 1 shown within a body vessel.

FIGS. 1 through 3 illustrate a delivery system, generally indicated at 10, according to the prior art. The delivery system comprises an elongate tubular member 12, such as a catheter, with a tapered distal end 14 and a proximal end 16 that includes one or more connectors 18. A lumen 20 runs the length of the elongate member 12 from the distal end 14 to the proximal end 16 and through the connector 18.

An expandable intraluminal device 22 is disposed circumferentially around a portion of the elongate member 12 near the distal end 14. Typically, the expandable intraluminal device 22 comprises a stent or other intraluminal device. A sheath 24 is circumferentially disposed around the elongate member 12 substantially along the entire length of the member 12. The sheath 24 is also disposed circumferentially around the expandable intraluminal device 22.

The prior art delivery system 10 is used to deliver and deploy the expandable intraluminal device 22 as follows. First, a user places a guidewire in a body vessel of a patient by navigating a distal end of the guidewire just beyond a point of treatment in the body vessel and leaving a proximal end of the guidewire outside of the patient. Next, with the sheath 24 disposed over the expandable intraluminal device 22, the user places the elongate member 12 over the placed guidewire by inserting the proximal end of the guidewire into the lumen 20 of the elongate member 12. The user then advances the elongate member 12 along the path in the body vessel established by the placed guidewire. Once the expandable intraluminal device 22 reaches a desired point of treatment in the body vessel, the user halts the advancement of the elongate member 12. Typically, this procedure is conducted in conjunction with an imaging technique to verify positioning of the expandable intraluminal device 22 at the desired point of treatment.

Once the desired position is reached, the user retracts the sheath 24 toward the proximal end 16 of the elongate member 12 while maintaining the position of the distal end 14 of the elongate member 12 relative to the point of treatment. The expandable intraluminal device 22 expands as the sheath 24 is retracted. After the sheath 24 is fully retracted from its position over the expandable intraluminal device 22, the device 22 expands along its entire axial length, freeing itself from its position with the elongate member 12.

FIG. 3 illustrates the prior art delivery system 10 within the lumen 52 of a body vessel 50. The delivery system 10 is depicted at a point in the delivery procedure prior to deployment of the expandable intraluminal device 22. Thus, the elongate member 12 is disposed circumferentially about the previously placed guidewire 40. Also, the sheath 24 has not been retracted and, accordingly, remains circumferentially disposed about the expandable intraluminal device 22.

As illustrated in FIG. 3, the delivery device 10 tends to orient near a wall surface 54 of the vessel 50 as opposed to remaining centrally, or substantially centrally, within the lumen 52 of the vessel 50. This orientation arises largely due to gravity, but torque on the elongate member 12 that arises during navigation through the body vessel 50 may also contribute to this orientation. If the expandable intraluminal device 22 does not include a functional mechanism that can be affected by a positioning near the wall surface 54, this tendency to orient toward the wall surface 54 of the vessel may not affect the performance of the expandable intraluminal device 22 following deployment. If, however, the expandable intraluminal device 22 includes such a mechanism, the prior art delivery method and device 10 might not provide a desirable positioning of the expandable intraluminal device 22 within the body vessel following deployment. For example, a functional mechanism of the expandable delivery device 22 may be oriented near or adjacent the wall surface 54 following deployment from the prior art delivery system 10. This may affect the ability of the functional mechanism to work properly, which may ultimately affect the overall performance of the expandable intraluminal device 22.

Several expandable intraluminal medical devices include a functional mechanism that can be affected by a positioning near a wall surface of a body vessel following deployment within the body vessel. For example, prosthetic venous valves include a valve mechanism that may not function optimally if the mechanism is positioned near or adjacent a wall surface of a body vessel following deployment. There are numerous types of prosthetic venous valves, and the methods and apparatuses described herein can be used with any suitable type of prosthetic venous valve. Examples of suitable prosthetic venous valves are described in U.S. Pat. No. 6,508,833 to Pavcnik for a MULTIPLE-SIDED INTRALUMINAL MEDICAL DEVICE, U.S. Patent Application Publication No. 2001/0039450 to Pavcnik for an IMPLANTABLE VASCULAR DEVICE, and U.S. patent application Ser. No. 10/642,372, filed on Aug. 15, 2003, each of which is hereby incorporated by reference in its entirety for the purpose of describing suitable prosthetic venous valves. It is noted, however, that the methods and apparatuses of the invention are not limited to prosthetic venous valves, nor are they limited to any particular type of expandable intraluminal device. Further, the expandable intraluminal device need not include any particular type of functional mechanism. The inventive methods and apparatuses can be used with any suitable expandable intraluminal device, including conventional stents.

Figure 4:
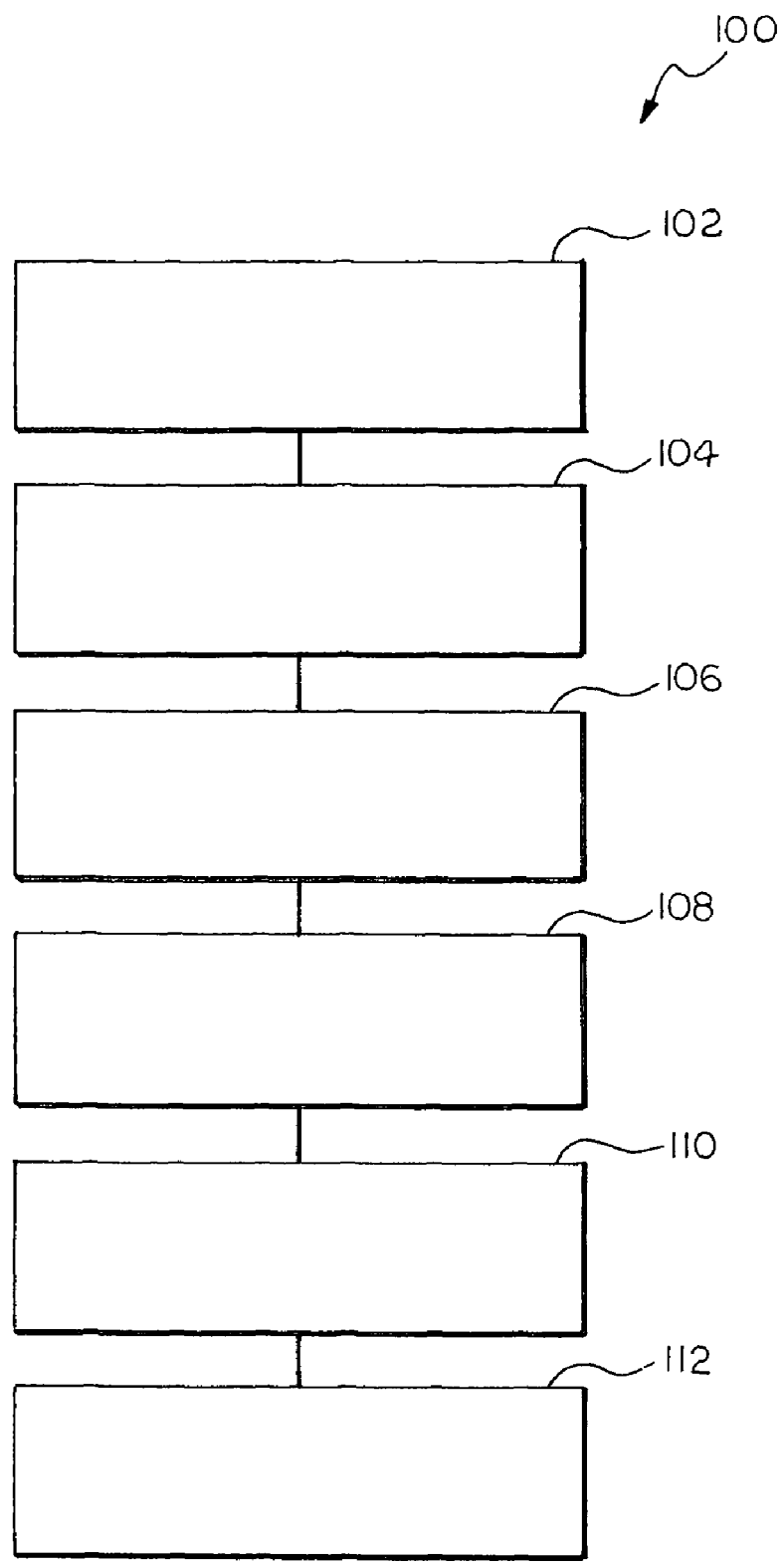
FIG. 4 is a flowchart of a method of deploying an expandable intraluminal medical device.

FIG. 4 illustrates a schematic of a new method 100 for delivering and deploying an expandable intraluminal medical device. In a first step 102 of the method 100, a user provides an elongate member that has an expandable intraluminal device disposed on a distal end of the elongate member. In another step 104, the user inserts the distal end of the elongate member into the lumen of a body vessel in a patient. In another step 106, the user advances the distal end of the elongate member through the lumen of the body vessel and to a desired point of treatment. The advancing of the elongate member can be conducted over a previously placed guidewire, but this is not required. In another step 108, the user spaces a portion of the elongate member from an interior wall surface of the body vessel. As used herein, the term "spaces," in the context of an action, refers to the act of setting two objects some distance apart relative to each other. Likewise, the term "spacing" refers to the same act, or as a descriptor of a structure suitable for use in such an act. The user can accomplish this step 108 using a variety of devices, as described herein. In another step 110, the user deploys the expandable intraluminal device at the point of treatment. This can be accomplished by retracting a sheath that is disposed around the expandable intraluminal device. In another step 112, the user withdraws the elongate member from the body vessel.

In practicing the method described above, a user can use a prior art delivery device, such as the device 10 illustrated in FIGS. 1 through 3. To accomplish the method with such a prior art device, the user must use the elongate member with an ancillary device that provides a means for spacing a portion of the elongate member from an interior wall surface of the body vessel. FIGS. 5 through 10 illustrate several suitable ancillary devices, each of which provides a means for spacing a portion of the elongate member from an interior wall surface of the body vessel.

FIG. 5 illustrates a basket device 60 used with the delivery system 10 illustrated in FIG. 1. The basket device 60 is a suitable means for spacing a portion of the elongate member 12 from an interior wall surface 54 of the body vessel 50. Baskets are known in the retrieval art and are commonly used to remove an object, such as a stone or other undesirable object, from a body cavity. Baskets have not been used, however, to space elongate members from vessel walls during deployment of an expandable intraluminal device from the elongate member.

FIG. 7 is a sectional view of the delivery system 10 and body vessel 50 illustrated in FIG. 5. The sectional view illustrates the spacing of the elongate member 12 from the vessel wall 54 that is achieved upon expansion of the basket device 60 (as illustrated in FIG. 5). The delivery system is substantially centered within the lumen 52 of the body vessel 50.

The basket device 60 includes an elongate main body 62 and a basket 64 formed at a distal end 66. The basket 64 includes a plurality of wire members 68 shaped into an enlarged formation relative to the main body 62. Open spaces 70 are interposed with the wire members 68. Attachment mechanisms 72, 74 collect the wire members 68 at proximal 76 and distal 78 ends of the basket 64, respectively. The wire members 68 are formed of a resilient material, such as nitinol, which can deform to allow the basket 64 to assume a collapsed configuration, i.e., a configuration with a reduced overall profile. This configuration allows the basket 64 to be collected into and navigated through the lumen 20 of the elongate member 12. The wire members 68 can have any suitable configuration, including round cross-sectional shapes. A flat wire can be used in the wire members 68, and is expected to provide desirable storage and vessel contact properties.

The basket device 60 can be used to space a portion of the elongate member 12 from an interior wall surface 54 of the body vessel 50 as follows. Once the elongate member 12 has been positioned within the lumen 52 of the body vessel 50, the guidewire (not illustrated in FIG. 5) is removed by retracting the guidewire through the lumen 20 of the elongate member 12. Next, the distal end 78 of the basket device 60 is inserted into the lumen 20 of the elongate member 12 at the proximal end (not illustrated in FIG. 5). The basket 64 is either in its collapsed configuration or is then placed into its collapsed configuration, and then advanced through the lumen 20. Once the basket 64 reaches the distal end 14 of the elongate member 12, the basket 64 is advanced out of the distal end 14. This causes the basket 64 to take its enlarged configuration, as illustrated in FIG. 5.

As a result of the enlargement of the basket 64, the elongate member 12 is spaced from an interior wall surface 54 of the body vessel 50 by a distance 80. The distance 80 can be any suitable distance, and the specific distance chosen will depend on numerous considerations, including the type of expandable intraluminal device being deployed. The distance 80 can correspond to a distance that places a geometric center of the expandable intraluminal device 22 at a geometric center of the body vessel 50, but this centering distance is not required. Further, the distance 80 need not be uniform around the entire inner circumference of the body vessel 50.

A difference between the new and prior art methods of delivering and deploying expandable intraluminal medical devices is shown by comparison of FIG. 5, illustrating the new method, and FIG. 3, illustrating the prior art method. Also, FIG. 6 illustrates the deployment of an expandable intraluminal medical device 22 according to the new method. In FIG. 6, the sheath 24 has been retracted and the expandable intraluminal medical device 22 has, as a result, been deployed. Because of the spacing of the elongate member 12 from the wall surface 54 provided by the basket 64, a functional mechanism 82 of the expandable intraluminal device 22 is spaced from an interior wall surface 54 of the vessel 50 by a distance 84. In FIG. 6, the expandable intraluminal device 22 comprises a prosthetic venous valve, and the functional mechanism 82 comprises the valve mechanism of the prosthetic valve 22. The spacing provided by the basket 64 positions the valve mechanism 80 near the geometric center of the vessel 50, which is expected to provide good function of the prosthetic valve 22.

Following deployment of the expandable intraluminal device 22, the basket 64 is drawn into the lumen 20 of the elongate member 12 while maintaining the position of the distal end 14 of the elongate member 12 relative to the expandable intraluminal device 22. The distal end 14 of the elongate member 12 forces the basket 64 into the collapsed configuration as the basket 64 is drawn into the lumen 20. The elongate member 12 is then withdrawn from the lumen 52 of the vessel 50. During this withdrawal, the distal end 14 of the elongate member 12 passes through the expandable intraluminal device 22.

FIG. 8 illustrates an alternative basket device 160. The basket device 160 is a suitable means for spacing an end of an elongate member (not illustrated in FIG. 8) from an interior wall surface of a body vessel. The basket device 160 is similar to the basket device 60 illustrated in FIG. 6, except as described below. Also, the basket device 160 is used in the same manner as the basket 60 illustrated in FIG. 6.

The basket device 160 includes a basket 164 formed from a plurality of wire members 168 disposed at a distal end 166 of a main body 162. At least one of the wire members 168 defines two or more commissural points 170. A section 172 of the wire member 168 connects adjacent commissural points 170. The commissural points 170 on each wire member 168 are the points of the wire member 168 that extend radially outward from the center of the basket 164 more than any other point of the wire member 168. The inclusion of multiple commissural points 170 in the wire members 168 allows for fewer points of contact between the wire members 168 of the basket 164 and a vessel wall while still providing the desired spacing effect.

FIG. 9 illustrates another alternate basket device 260. The basket device 260 is a suitable means for spacing an end of an elongate member (not illustrated in FIG. 9) from an interior wall surface of a body vessel. The basket device 260 is similar to the basket device 160 illustrated in FIG. 8, except as described below. Also, the basket device 260 is used in the same manner as the basket 160 illustrated in FIG. 8.

The basket device 260 includes a basket 264 formed of four wire members 268. Each wire member 268 defines two commissural points 270.

FIG. 10 illustrates an alternate basket device 360 with the elongate member 10. The basket device 360 is a suitable means for spacing an end of the elongate member 12 from an interior wall surface 54 of the body vessel 50. The basket device 360 includes a basket 364 formed from a plurality of wire members 368 and is disposed at a distal end 366 of a main body 362. In this embodiment, a portion of each wire member 368 is folded back to overlap the distal end 14 of the elongate member 12 when the basket 364 is in its expanded configuration. This arrangement positions a vessel wall contacting portion 370 of the wire members 368 in closer proximity to the distal end 14 of the elongate member 12 than other embodiments that lack this arrangement. As a result, the portion of the elongate member 12 that is spaced from the wall surface 54 of the body vessel 50 is extended proximally along the elongate member 12 (to the left in FIG. 10). This arrangement of the wire members 368 may provide a more effective means for spacing a portion of the elongate member 12 from the wall surface 54 of the body vessel 50.

The wire members 358 can be formed so that the basket 364 does not include the folded back arrangement when the basket 364 is in the collapsed configuration (i.e., disposed within the elongate member 12). Also, any suitable configuration of the wire members 358 that achieves the folded-back arrangement can be used to form the basket 364. In one suitable configuration, each wire member 358, when the basket is in its expanded configuration, includes first and second 180° turns that are offset by 90° relative to each other.

FIG. 11 illustrates a delivery device 400 that can be used with the method illustrated in FIG. 4. The delivery device 400 comprises an elongate member 402 having a main body 404, and proximal 406 and distal 408 ends. In the illustrated embodiment, the elongate member 402 comprises a catheter. The distal end 408 defines a tapered or rounded end 410. An expandable intraluminal device 412 is circumferentially disposed about the main body 404 near the distal end 408. A sheath 414 is circumferentially disposed around the expandable intraluminal device 412 and extends substantially along the length of the elongate member 402 from the proximal end 406 to the distal end 408. The sheath 414 can be moved axially along the elongate member 402.

In this embodiment, the elongate member 402 includes a means for spacing a portion of the elongate member 402 from an interior wall surface of a body vessel. In contrast to the embodiments illustrated in FIGS. 5 through 10, the means for spacing in this embodiment is an integral part of the elongate member 402, and is not a separate ancillary device. This embodiment eliminates the need for exchanging a placed guidewire with an ancillary device that provides the needed means for spacing.

The elongate member 402 illustrated in FIG. 11 includes a Malecot assembly 416. The Malecot assembly is a suitable means for spacing a portion of the elongate member 402 from an interior wall surface of a body vessel. Malecot assemblies are known in the medical technology art and are commonly used to provide drainage egress from a body cavity. Malecot assemblies have not, however, been used as a means for spacing a portion of an elongate member from a wall surface of a body vessel. U.S. Pat. No. 2,649,092 provides a description of a Malecot assembly, and is incorporated by reference into this disclosure in its entirety for the purpose of describing a Malecot assembly.

Briefly, the Malecot assembly 416 comprises two or more strip-like sections 418 of material that are formed by slits in the material of the elongate member 402. An elongate activator 420 is attached to the distal end 408 of the elongate member and extends through the elongate member 402 to the proximal end 406. To activate the Malecot assembly 416, a user pulls the elongate activator 420 toward the proximal end 406 of the elongate member 402. This action enlarges the slits in the elongate member 402 to create open spaces 422 and force the strip-like sections 418 to fold and extend radially outward. The radially-outward extending strip-like sections 418 of material space the elongate member 402 from a surface contacting a fold 424 in the sections 418, such as an interior wall surface of a body vessel. To deactivate the Malecot assembly and substantially return the strip-like sections 418 to their original position, the user releases the elongate activator 420. A pusher (not illustrated) can be advanced through the lumen of the elongate member 402 to push on the distal end 408 to facilitate deactivation of the Malecot assembly 416.

During advancement of the distal end 408 of the elongate member 402, the sheath 414 can be circumferentially disposed about the Malecot assembly 416 (in its unactivated configuration) and the expandable intraluminal device 412. To deploy the expandable intraluminal device 412, the sheath 414 can be retracted to a first position axially interposed between the Malecot assembly 416 and the expandable intraluminal device 412. The Malecot assembly 416 is then activated to accomplish the desired spacing. Then, the expandable intraluminal device 412 is deployed by further retracting the sheath 414 from its position over the device 412. Lastly, the Malecot assembly 416 is deactivated and the entire delivery device 400 is withdrawn from the body vessel. During withdrawal, the distal end 408 passes through the deployed expandable intraluminal device 412.

The delivery device 400 can be used with or without a previously placed guidewire.

FIG. 12 illustrates a delivery device 500 that can be used in the method illustrated in FIG. 4. The delivery device 500 comprises an elongate member 502 having a main body 504, and proximal 506 and distal 508 ends. In the illustrated embodiment, the elongate member 502 comprises a catheter. The distal end 508 defines a tapered or rounded end 510. An expandable intraluminal device 512 is circumferentially disposed about the main body 504 near the distal end 508. A sheath 514 is circumferentially disposed around the expandable intraluminal device 512 and extends substantially along the length of the elongate member 502 from the proximal end 506 to the distal end 508.

Similar to the embodiment illustrated in FIG. 11, the elongate member 512 includes a means for spacing a portion of the elongate member 502 from an interior wall surface of a body vessel. This embodiment also stands in contrast to those illustrated in FIGS. 5 through 10 in that the means for spacing is an integral part of the elongate member 502 and not a separate ancillary device.

In this embodiment, the elongate member 502 includes an inflatable balloon 516. The balloon 516 is inflated by passing a fluid, such as saline, through an inflation lumen (not illustrated) in the elongate member 502. The inflation of the balloon 516 provides the desired spacing of a portion of the elongate member 502 from the vessel wall. The balloon 516 is deflated by removing the fluid from the balloon 516. The balloon 516 is positioned distal to the expandable intraluminal device 512 on the elongate member 502.

During advancement of the distal end 508 of the elongate member 502, the sheath 514 can be circumferentially disposed about the balloon 516 (in its uninflated configuration) and the expandable intraluminal device 512. To deploy the expandable intraluminal device 512, the sheath 514 can be retracted to a first position axially interposed between the balloon 516 and the expandable intraluminal device 512. The balloon 516 is then inflated to accomplish the desired spacing. Then, the expandable intraluminal device 512 is deployed by further retracting the sheath 514 from its position over the device 512. Lastly, the balloon 516 is deflated and the entire delivery device 500 is withdrawn from the body vessel. During withdrawal, the distal end 508 of the elongate member 502 passes through the deployed expandable intraluminal device 512.

The delivery device 500 can be used with or without a previously placed guidewire (not illustrated).

FIGS. 13 and 14 illustrate a delivery device 600 that can be used in the method illustrated in FIG. 4. The delivery device 600 of this embodiment is similar to the embodiment illustrated in FIGS. 5 and 6, except as described below. Thus, the delivery device 600 includes an elongate member 602 having proximal (not illustrated) and distal 604 ends. An expandable intraluminal device 606 is disposed circumferentially about a portion of the elongate member 602. A sheath 608 is circumferentially disposed about the elongate member 602 and can be moved axially along the length of the elongate member 602. The elongate member 602 defines an ancillary lumen 610 that extends from the distal end 602 to the proximal end. An ancillary device 612 is disposed in the ancillary lumen 610 and includes a means for spacing a portion of the elongate member 602 from an interior wall surface of a body vessel. In the illustrated embodiment, the means for spacing comprises a basket 614 but any suitable means for spacing can be used.

The elongate member 602 also defines a guidewire lumen 616 that extends along the length of the elongate member 602 from the proximal end to the distal end 604. The guidewire lumen 616 is separate from the ancillary lumen 610. A guidewire 618 is disposed in the guidewire lumen 616 when the delivery device 600 is advanced over a previously placed guidewire 618.

The delivery system 600 avoids the need for exchanging a placed guidewire with an ancillary device that provides the needed means for spacing. Rather, the guidewire 618 can be left in place prior to, during, and following activation of the means for spacing.

To use this delivery system 600 in the method illustrated in FIG. 4, the delivery device 600 is advanced over a previously placed guidewire 618 to a desired point of treatment in a body vessel 620. The delivery system 600 is advanced by passing the guidewire 618 through the guidewire lumen 616. Once the desired point of treatment is reached, the means for spacing is activated to accomplish the desired spacing. In this embodiment, the basket 614 is advanced out of the ancillary lumen 610, which causes the basket 614 to expand and space the elongate member 602 from the interior wall 622 of the body vessel 620. The sheath 608 is retracted to deploy the expandable intraluminal device 606.

Following deployment, the basket 614 is retracted into the ancillary lumen 610, forcing it to collapse. Then the delivery device 600 is withdrawn from the body vessel, passing the distal end 604 through the deployed expandable intraluminal device 606. The guidewire 618 can be withdrawn with the elongate member 602 and sheath 608, as one unit, or separately following withdrawal of these components.

Figure 15:
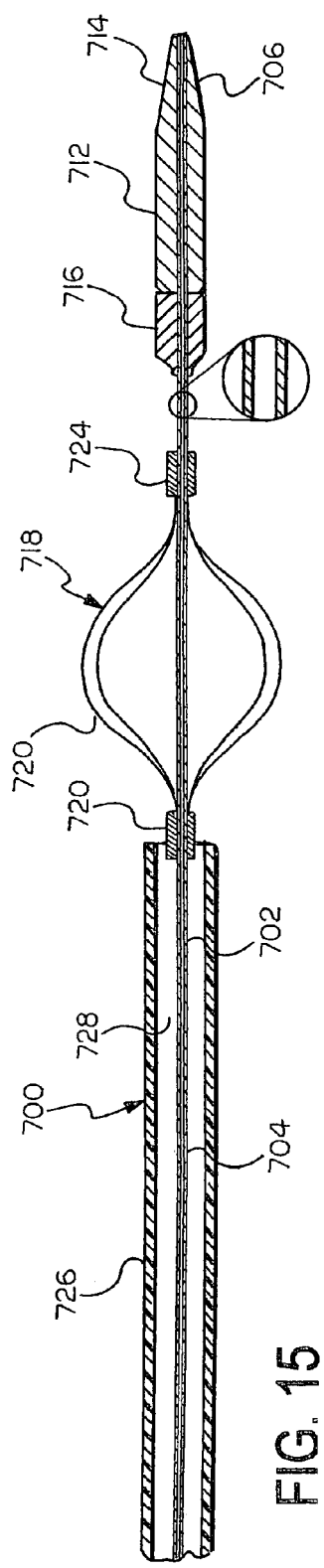
FIG. 15 is a sectional view of a delivery system according to an embodiment of the invention.

FIG. 15 illustrates a delivery device 700 that can be used in the method illustrated in FIG. 4. The delivery device 700 of this embodiment includes an elongate cannula 702 that has a main body 704 and proximal (not illustrated) and distal 706 ends. The cannula 708 defines a lumen 710 through which a guidewire (not illustrated in FIG. 15) can be passed. A distal nose piece 712 is attached to the distal end 706 of the cannula 702 and defines a tapered or rounded surface 714. A sheath stop 716 is also attached to the cannula 702 and is disposed proximal to the distal nose piece 712 in abutting relationship.

A means for spacing a portion of the elongate cannula 702 is also attached to the elongate cannula 702. In the illustrated embodiment, the means for spacing comprises a basket 718, but any suitable means for spacing can be used. The basket 718 includes a plurality of resilient wire members 720. Proximal 722 and distal 724 attachment mechanisms collect the wire members 720 and attach the basket 718 to the cannula 702. In the illustrated embodiment, the attachment members 720, 724 comprise cannulae that are circumferentially disposed around the main body 704 of the cannula 702. The proximal attachment mechanism 722 is fixedly attached to the cannula 702, while the distal attachment mechanism 724 is slideably disposed about the elongate member 702. The distal attachment mechanism 724 moves over a portion of the elongate member 702 as the basket 718 expands radially outward and contracts radially inward.

An elongate tubular sheath 726 is circumferentially disposed about the elongate cannula 702. The sheath 726 defines an interior passageway 728. The passageway 728 has an interior diameter that permits the basket 718 to be stored within the passageway 728 in a radially contracted configuration. Also, the sheath stop 716 has an outer diameter that creates a snug fit between the sheath stop 716 and the sheath 726 when the sheath 726 is passed over the sheath stop 716. This secures the delivery system 700 in a storage configuration in which the basket is radially contracted.

The sheath 726 effects the expansion and contraction of the basket 718 through its axial movement along the cannula 702. As the sheath 726 is retracted off the sheath stop 716 and over the basket 718, the basket 718 expands radially outward, giving the configuration illustrated in FIG. 15. To return the basket 718 to its radially contracted configuration, the sheath 726 is advanced over the basket 718, forcing the distal attachment mechanism 724 to advance distally over the cannula 702. Ultimately, the sheath 726 can be advanced over the sheath stop 716 to establish the snug fit and return the delivery system 700 to its storage configuration.

Figure 16A:
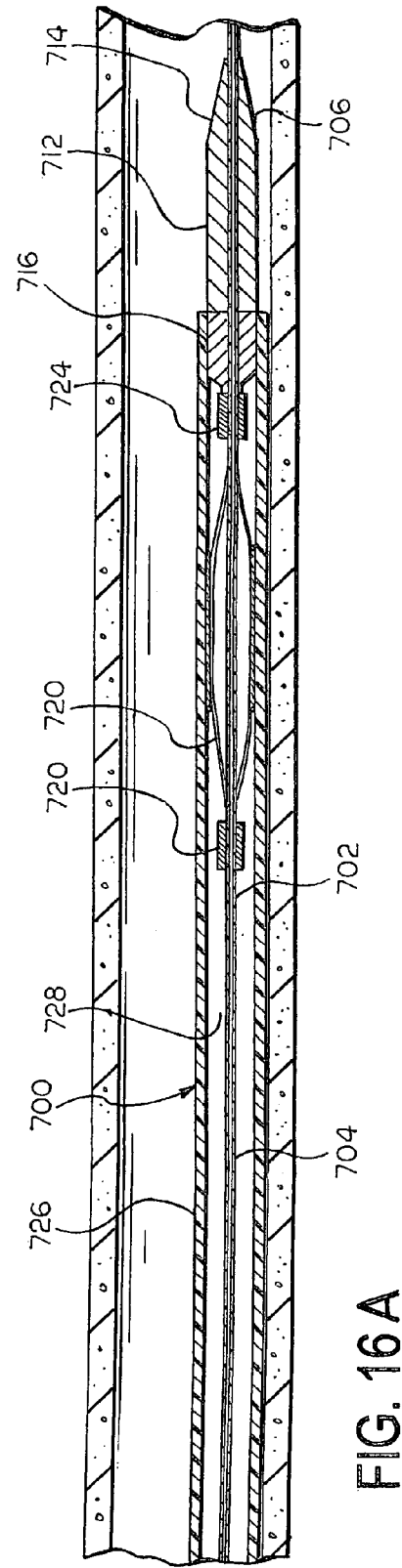
FIG. 16A is a sectional view of the delivery system illustrated in FIG. 15 shown within a body vessel and at an initial stage of deployment of an expandable intraluminal medical device.

FIGS. 16A, 16B, 16C, and 16D illustrate the deployment of an expandable intraluminal device 730 using the delivery system 700 illustrated in FIG. 15. In FIG. 16A, the delivery system 700 is disposed over a previously placed guidewire 732 within the lumen 734 of a body vessel 736. The delivery system 700 has been advanced through the body vessel 736 along the guidewire 732. The guidewire 732 extends through the lumen 710 of the cannula 702.

In the illustrated embodiment, the expandable intraluminal device 730 is circumferentially disposed about the basket 718 within the passageway 728 of the sheath 726. In this arrangement, the basket 718 provides the desired spacing function, and also acts to assist in seating the expandable intraluminal device 730 within the vessel 736. As with all embodiments, the expandable intraluminal device 730 can be any suitable expandable intraluminal device. In the illustrated embodiment, the expandable intraluminal device 730 comprises a prosthetic venous valve.

As illustrated in FIG. 16A, the sheath 726 of the delivery system 700 is positioned adjacent an internal wall surface 738 of the vessel 736 upon initial placement within the vessel 736.

In FIG. 16B, a portion of the cannula 702 and other portions of the delivery system 700 have been spaced from the internal wall surface 738 of the body vessel 736 by the basket 718. The sheath 726 has been axially retracted over the basket 718 to effect its radial expansion. The radial expansion of the basket also forces a portion of the expandable intraluminal device 730 against the interior wall surface 738 of the body vessel 736. This is expected to enhance the seating of the device 730 within the vessel 736, perhaps by driving barbs or other anchoring mechanisms (not illustrated) into the vessel wall 738. The distal attachment mechanism 724 has moved proximally over the cannula 702 to accommodate the expansion of the basket 718.

In FIG. 16C, the sheath 726 has been advanced distally, contacting the basket 718 and forcing its radial contraction. The distal attachment mechanism 726 has moved distally over the cannula 702 to accommodate the contraction of the basket 718.

Figure 16D:
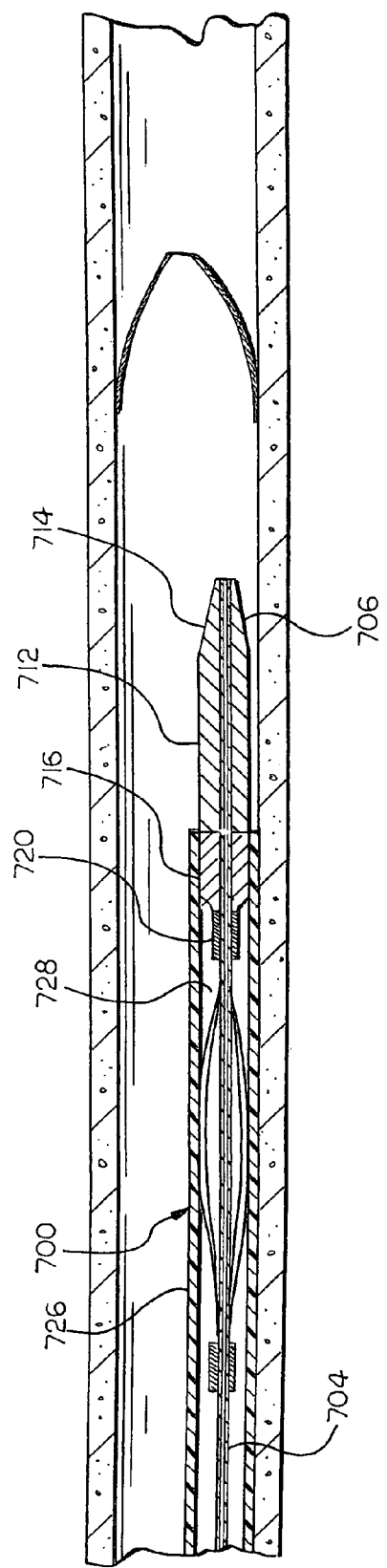
FIG. 16D is a sectional view of the delivery system illustrated in FIG. 15 shown within a body vessel and at a subsequent stage of deployment of an expandable intraluminal medical device.

To complete the deployment of the expandable intraluminal device 730, the sheath 726 is advanced completely over the basket 718 and over the sheath stop 716 to restore the snug fit between the sheath 726 and the sheath stop 716. The delivery device 700, including the cannula 702, is then withdrawn from the vessel 736. During the withdrawal, the distal end of the delivery system 700, including the distal nose piece 712, is drawn through the now expanded expandable intraluminal device 730. FIG. 16D illustrates the delivery system 700 just after deployment of the expandable intraluminal device 730 and the initiation of withdrawal of the delivery device 700 from the body vessel 736. The sheath 726 is again disposed adjacent the interior wall surface 738 of the body vessel due to the contraction of the basket 718.

The preceding detailed description includes the best mode for practicing the invention. The methods and embodiment described herein are exemplary in nature, and are not intended to limit the scope of any claims.

We claim:

1. A method for delivering and deploying an expandable intraluminal medical device, comprising:
    providing a delivery system comprising an elongate member having proximal and distal ends and defining a lumen, the delivery system further comprising an ancillary delivery device adapted to be inserted into and advanced through the lumen and having a means for spacing a portion of the elongate member from a wall surface of a body vessel, said expandable intraluminal medical device circumferentially disposed about a portion of the elongate member and having a distal end, said means for spacing having a proximal end and a distal end;
    the means for spacing comprising a basket formed from at least two wire members having expanded and collapsed configurations, each of the at least two wire members having a proximal wire end and a distal wire end, the at least two wire members not crossing each other and contacting each other only at the respective proximal and distal wire ends to define open spaces between the at least two wire members;
    placing a guidewire in the body vessel;
    inserting the distal end of the elongate member over the guidewire and into the body vessel;
    advancing the distal end of the elongate member over the guidewire and through the body vessel and to a desired point of treatment;
    removing the guidewire from the body vessel by retracting the guidewire through the lumen of the elongate member;
    inserting the ancillary delivery device into the proximal end of the elongate member and into the lumen;
    advancing the ancillary delivery device through the lumen until the means for spacing exits the distal end of the elongate member;
    spacing a portion of the elongate member from a wall surface of the body vessel at a point distal to said expandable intraluminal medical device by activating the means for spacing such that an axial portion of the elongate member disposed between the proximal end of the means for spacing and the distal end of the intraluminal medical device is free of contact with the wall surface of the body vessel;
    deploying said expandable intraluminal medical device from the elongate member while the elongate member is being spaced from a wall surface of the body vessel;
    retracting the means for spacing into the lumen of the elongate member while maintaining the position of the distal end of the elongate member relative to the deployed expandable intraluminal medical device; and
    withdrawing the elongate member from the body vessel;
    wherein the deploying step is performed while the spacing step is being performed.

2. The method for delivering and deploying an expandable intraluminal medical device according to claim 1, wherein the step of spacing a portion of the elongate member from a wall surface of the body vessel comprises spacing a portion of the elongate member that includes said expandable intraluminal medical device.

3. The method for delivering and deploying an expandable intraluminal medical device according to claim 1, wherein the delivery system further comprises a sheath circumferentially disposed about the elongate member and movable along the elongate member, and wherein the step of deploying the expandable intraluminal medical device comprises retracting the sheath from a position about the expandable intraluminal medical device.

4. The method for delivering and deploying an expandable intraluminal medical device according to claim 3, wherein the activating the means for spacing includes retracting the sheath from a position about the means for spacing.

5. The method for delivering and deploying an expandable intraluminal medical device according to claim 1, wherein said expandable intraluminal medical device comprises a prosthetic venous valve.

* * * * *

UNITED STATES PATENT AND TRADEMARK OFFICE
CERTIFICATE OF CORRECTION

| | | |
|---|---|---|
| PATENT NO. | : 7,909,862 B2 | Page 1 of 1 |
| APPLICATION NO. | : 10/804386 | |
| DATED | : March 22, 2011 | |
| INVENTOR(S) | : Michael L. Garrison et al. | |

It is certified that error appears in the above-identified patent and that said Letters Patent is hereby corrected as shown below:

Title page, Item (73) Assignee; Two Assignees should be listed in (73) Assignee as follows:

Cook Medical Technologies LLC, Bloomington, IN (US)

Oregon Health & Science University, Portland, OR (US)

Signed and Sealed this
Twenty-sixth Day of April, 2011

David J. Kappos
*Director of the United States Patent and Trademark Office*